United States Patent [19]
van't Hooft

[11] Patent Number: 5,503,041
[45] Date of Patent: Apr. 2, 1996

[54] APPARATUS FOR CONNECTING A FIRST END PART OF A CABLE TO A DRIVE UNIT

[75] Inventor: Eric van't Hooft, Leersum, Netherlands

[73] Assignee: B.V. Optische Industrie "De Oude Delft", Delft, Netherlands

[21] Appl. No.: 92,694

[22] Filed: Jun. 25, 1993

[30] Foreign Application Priority Data

Jun. 25, 1992 [NL] Netherlands ............................ 9201131

[51] Int. Cl.$^6$ ................................ F16C 1/14; A61N 5/01
[52] U.S. Cl. ...................... 74/502.6; 74/500.5; 250/497.1
[58] Field of Search .................. 74/89.2, 500.5, 74/502.4, 502.6; 600/1, 3, 6, 7; 250/497.1, 494.1

[56] References Cited

U.S. PATENT DOCUMENTS

| | | | |
|---|---|---|---|
| 3,593,594 | 7/1971 | Perry ................... | 74/502.6 X |
| 4,281,252 | 7/1981 | Parsons, Jr. et al. ............. | 74/502.6 X |
| 4,314,157 | 2/1982 | Gaines ................... | 250/497.1 |
| 4,412,499 | 11/1983 | Hall . | |
| 4,649,658 | 3/1987 | Sarton et al. . | |
| 4,881,937 | 11/1989 | van'Houft et al. .......... | 600/3 |

FOREIGN PATENT DOCUMENTS

| | | |
|---|---|---|
| 0152124 | 8/1985 | European Pat. Off. . |
| 0474994 | 3/1992 | European Pat. Off. . |
| 2248283 | 4/1992 | United Kingdom . |

*Primary Examiner*—Richard M. Lorence
*Attorney, Agent, or Firm*—Griffin, Butler, Whisenhunt & Kurtossy

[57] ABSTRACT

A method and apparatus for connecting a first end part of a cable to a drive unit, this cable carrying at its second end part an element, such as a source of radiation, which can be moved through a guide tube, wherein there are provided at least two first end parts with a different mechanical identification in the form of recesses, thickenings, projections or the like, and there being provided a number of different connector elements, corresponding to the number of different end parts, the connector elements each having locking means which can only cooperate with an end part provided with a particular mechanical identification, whilst a cable with a first end part provided with a mechanical identification associated with the desired element to be displaced is chosen and is inserted into a matching connector element, whereafter the first end part is locked in the relevant connector element by means of the locking means.

10 Claims, 9 Drawing Sheets

APPARATUS FOR CONNECTING A FIRST END PART OF A CABLE TO A DRIVE UNIT

This invention relates to a method for connecting a first end part of a cable to a drive unit, this cable carrying at its second end part an element, such as a source of radiation, which can be moved back and forth through a guide tube, in which method the first end part is inserted into a connector element belonging to the drive unit and is locked by means of locking means, and to an assembly, a drive unit and a cable for carrying out such method.

BACKGROUND OF THE INVENTION

For the local irradiation of tumors, use is made of hollow needles to be introduced into the body, which needles are closed at one end and connect to a guide tube by their other end. A source of radiation with predetermined properties, such as the intensity, is attached to one end of a cable and, by means of that cable, can be brought from a shielded container via the guide tube into a predetermined position in the hollow needle and from that position back again into the shielded container. The displacement of a cable having a source of radiation at its one end is typically effected by connecting the other end of that cable to a drive unit which imposes a displacement on the cable such that the cable end with the radiation source is displaced through the guide tube into the needle. To that end, the other end can be coupled to a rotary drum, the cable end with the source of radiation being displaced by winding the cable onto the drum or unwinding it therefrom. The coupling of the other cable end to the drive unit is typically effected by locking the other cable end with locking means.

Often, a tumor is irradiated from more than one side and, accordingly, a plurality of needles may be present and optionally different sources of radiation may be present in the different needles. In this connection, it is of great importance that the proper source of radiation with the desired intensity and form ends up at a predetermined site. This requires close attention on the part of the operating staff. Choosing and mounting the correct source of radiation is naturally of equally great importance if only one needle and one source of radiation are used.

The object of the invention is to provide a guarantee, when working with such equipment, that the source of radiation coupled with a drive unit by means of a cable is in fact the intended source of radiation.

SUMMARY OF THE INVENTION

According to the invention, this is realized in a method of the type described in the preamble, in that there are provided at least two first end parts with a different mechanical identification in the form of recesses, thickenings, projections or the like, a first end part of a particular mechanical identification being characteristic of a particular type of element to be displaced, such as a source of a particular intensity and form, and that there are provided a number of different connector elements, corresponding to the number of different end parts, the connector elements each having locking means which can only cooperate with an end part provided with a particular mechanical identification, whilst a cable with a first end part provided with a mechanical identification associated with the desired element to be displaced is chosen and is inserted into a matching connector element, whereafter said first end part is locked in the relevant connector element by means of the locking means.

Through these measures, it is ensured that always the correct source of radiation is connected to a particular drive unit, because a cable end with a non-matching mechanical identification cannot be locked. The mechanical identification at the other cable end has a further advantage in that a visual means of recognition is present which can prevent any attempts to fit any other cable end that does not match the connector element.

An additional guarantee can be realized if, in accordance with a further embodiment of the invention, the locking means are formed by a stop member and a movable member, whilst a first end part to be introduced is first positioned by the stop member and then locked in that position by the movable member. Through these measures, a further aid is provided in preventing a cable with a non-intended source of radiation being fitted, because the stop gives a defined position either allowing or disallowing the locking means to be brought into their locking position.

The mechanical identification can be designed in a variety of ways. A first possibility is to provide a cylindrical element at the other end of the cable, the diameter of that element constituting the mechanical identification. Another possibility is to provide a collar, whose diameter, thickness and/or location is characteristic of the source of radiation affixed to one end. In accordance with a further embodiment of the invention, however, it is preferred that the mechanical identification is formed by a circumferential recess provided in the first end part, the distance from this recess to the free end of the first end part constituting the mechanical identification of the cable, the stop member of the locking means is provided with a bore, which has a cross-section such that the first end part can be received therein with a sliding fit and has a depth which determines which mechanically identified first end part can be locked by the locking means, and the movable member of the locking means is formed by a guided element capable of moving transversely to the bore, this element comprising a part having a width substantially corresponding to the length of the circumferential recess in the first end part and comprising a slot, open at one end, of a width corresponding to the diameter of the first end part at the recess, the locking of the first end part being effected by inserting the first end part with a mechanical identification associated with the depth of the bore in the stop member of the locking means, into that bore until it is stopped, and subsequently moving the movable member such that the recess in the first end part ends up in the slot, whereby the first end part is locked in the position where it has been stopped in the bore. Through these measures, it is ensured in a relatively simple, yet particularly effective manner, that only a cable with the correct identification can be fitted. If a cable with an incorrect mechanical identification is used, then the recess in the stop position will either be situated in the bore or be located before the bore at such a distance that the locking means cannot be brought into their locking position because the end of the open slot faces a part of the other cable end that has a cross-section greater than the width of the slot. Any movement of the locking means is then impossible, which not only prevents the locking action but also provides a clear, visual indication that an incorrect cable has been used.

The invention further relates to an assembly of a drive unit and a cable secured therein through a first end thereof, this cable being provided at the second end thereof with an element to be displaced, such as a source of radiation, the drive unit comprising a connector element with receiving means and locking means for positioning and locking the first end to be locked, which ends in a cylindrical element.

With such an assembly, in order to prevent the mounting of a cable with a non-intended element attached thereto, it is proposed, in accordance with the invention, that the receiving means comprise a stop member with a bore which can receive the cylindrical element with a sliding fit and has a bottom surface which forms a stop surface for the cylindrical element, and that the locking means can be moved relatively to the connector element according to a predetermined path and can cooperate with mechanical identification means in the form of recesses, thickenings, projections, or the like, provided on or near the cylindrical element, there being provided a plurality of different and mutually exchangeable connector elements and, of each connector element, the dimensions of the bore and the location of the locking means in mutual conjunction determine with which design of the mechanical identification means cooperation can be effected, a further preference being expressed to the effect that with all connector elements, the location and displacement of the locking means are equal, whilst the dimensions of the bores are different with each connector element. In this way, the object contemplated is achieved with simple means that are relatively simple to fit, inter alia because the locking means can always be of identical design.

If, in accordance with a further embodiment of the invention, the diameter of the bore is equal in all connector elements, whilst the depth of the bores is different in each connector element, the provision of a one-on-one locking arrangement only requires that the depth of the bore and the location of the recess be different whilst all of the other parts can be equal.

The locking arrangement can be realized in a particularly reliable manner, if the mechanical identification means at a first end consist of a circumferential recess, which, for the purpose of locking the first cable end, can cooperate with an open slot in a part belonging to the locking means, which part can be moved in the longitudinal direction of the open slot between a position outside the path of a first end to be inserted and locked, and a position wherein that end is locked, for which purpose the open slot is provided with a bottom which engages in the recess so as to lock the end. In this manner, a form-closing cooperation between recess and slot is obtained, which is not only locked particularly effectively, but also, owing to the requirement of trilateral form closure, constitutes an additional safeguard against the possibility of an incorrect cable being fitted.

A further guarantee of a one-on-one cooperation is obtained if the stop member is resiliently mounted for movement between a resiliently decompressed and a resiliently compressed position. By choosing the resiliently compressed position as the stop position wherein the locking means can be brought into locking engagement, the locking means can be prevented from being moved to their locking position without the other cable end being disposed in its stop position. This safeguard can be further perfected if the locking means comprising the part with the open slot are resiliently mounted in the connector element so as to be movable in the longitudinal direction of the open slot, the stop element being disposed outside the path of the locking means in the resiliently compressed position and within the path of the locking means in the resiliently decompressed position.

It has already been observed that locking means not disposed in their locking position give a visual indication of an as yet unaccomplished coupling or a non-realizable coupling. Use can be made of this, in a further advantageous manner, if the locking means are provided with a pawl-shaped part, which does form a projection of the connector element in the case where the bottom of the open slot is not in locking cooperative engagement with the recess, and which does not form a projection of the connector element in the case where the bottom of the open slot is in locking cooperative engagement with the recess, the pawl-shaped part in its projecting position blocking the normal operation of the drive unit. In this way it is ensured that under all circumstances, it is impossible to work with a non-locked cable end and, accordingly, with a cable provided with a non-intended source of radiation.

BRIEF DESCRIPTION OF THE DRAWINGS

With reference to the embodiments shown in the drawings, the method and the assembly according to the invention will now be further discussed and explained. In these drawings.

DESCRIPTION OF PREFERRED EMBODIMENTS

Figure 1:
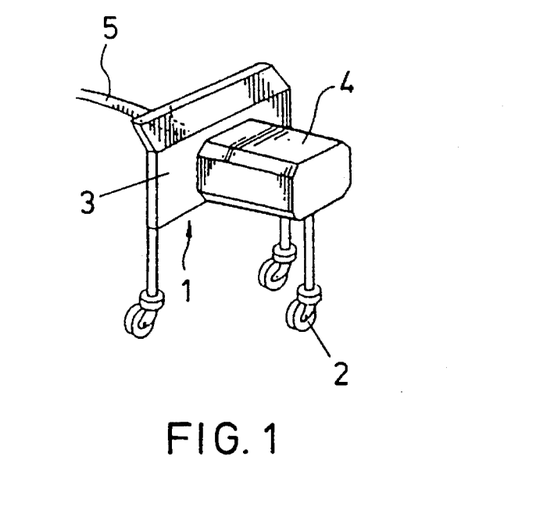
FIG. 1 schematically shows an apparatus to be used for the local irradiation of a tumor.

FIG. 1, by way of example only, schematically shows an apparatus 1 for the local irradiation of a tumor, which apparatus comprises a frame 3 which can be moved by means of wheels 2 and may comprise operating means and a control panel (not shown). Further, the frame 3 carries a container 4 which may accommodate radioactive material in a shielded manner. The radioactive material is arranged at one end of a cable and thus can be moved by and along with that cable via a drive unit, through a guide tube 5 running to the patient to be treated, this tube 5 being in communication with the container 4, to which several guide tubes, which may or may not be surrounded by a common sheath, may be connected.

Figure 2:
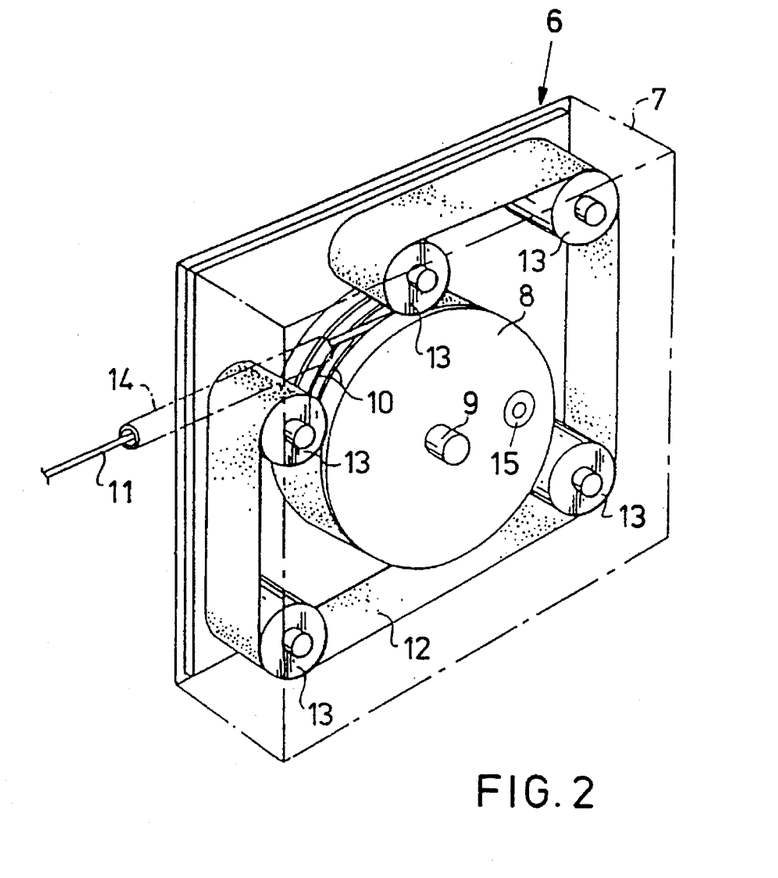
FIG. 2 shows a drive unit for a cable to be moved through a guide tube.

FIG. 2 shows a drive unit 6 to be used with the apparatus according to FIG. 1, this drive unit 6 comprising a housing 7, largely depicted transparently to render visible a number of components accommodated within the housing.

In the housing 6, a drum 8 with a cylindrical circumferential surface is arranged for rotation about a shaft 9. Provided in the cylindrical circumferential surface is a helical groove 10, permitting a cable 11 to be wound onto and off the drum. The cable 11 is kept in accurate and slip-free contact with groove 10 by means of an endless belt 12 passing around rollers 13. From the drum 8, the cable 11 is directed through a covering 14 which connects to a shielded storage element for the radioactive material attached to one end of the cable 11, the other end thereof being coupled with the drum 8 by means of a connector element 15. The covering 14 connects to the guide tube 5 with or without interruption.

Figure 3:
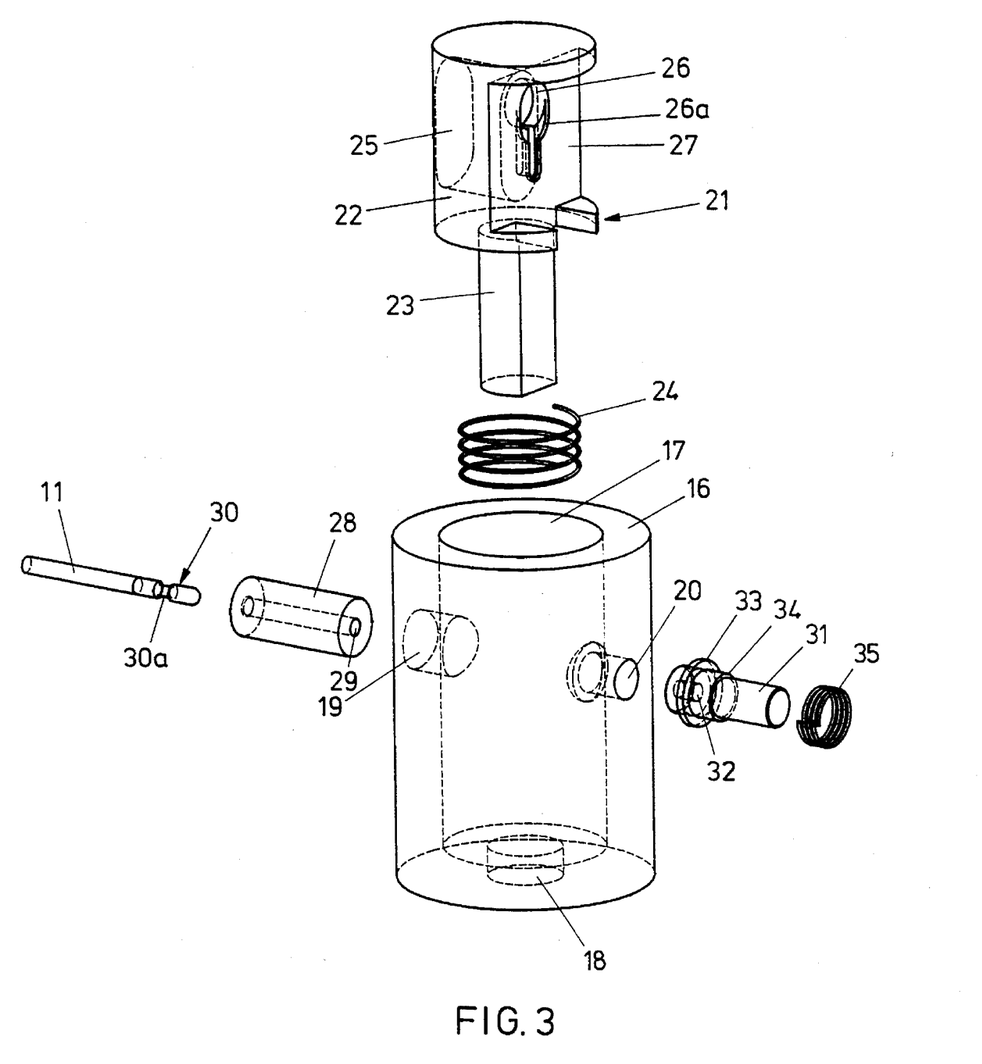
FIG. 3 shows an exploded view of a connector element to be utilized in a drive unit according to FIG. 2.

FIG. 3 is an exploded view of a first embodiment of a connector element 15, comprising a shell-shaped housing part 16, which is provided with a central bore 17, which extends from one end of the housing part 16 as far as near the other end, where it merges in a stepped manner with a bore 18 which is in line with the central bore 17. The housing part 16 further comprises a receiving bore 19 and a sliding bore 20, the common centreline of the bores 19 and 20 intersecting the centreline of the central bore 17 at right angles. A locking member 21 comprises a cylindrical part 22 which can be received by the central bore 17 with a sliding fit, and a flattened cylindrical part 23 which can be received in the passage 18 with a sliding fit. By arranging a spring 24 around the flattened cylindrical part 23, the locking member 21 can be accommodated in the housing part 16 for resilient movement, the flattened cylindrical part 23 reaching throught the bore 18.

Figure 4:
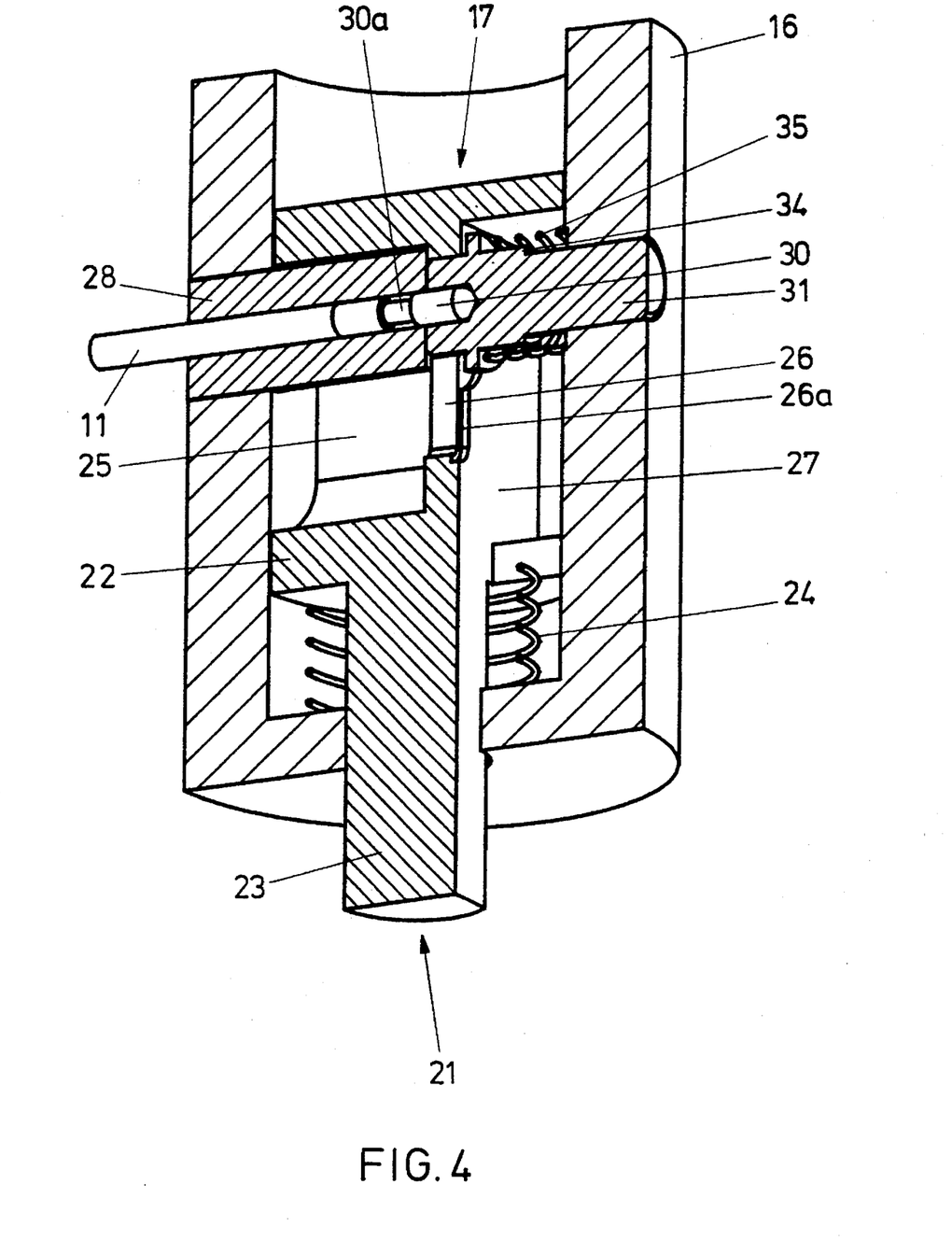
FIG. 4 shows a cross-section of the connector element according to FIG. 3 in assembled form in a first assembly position.
Figure 5:
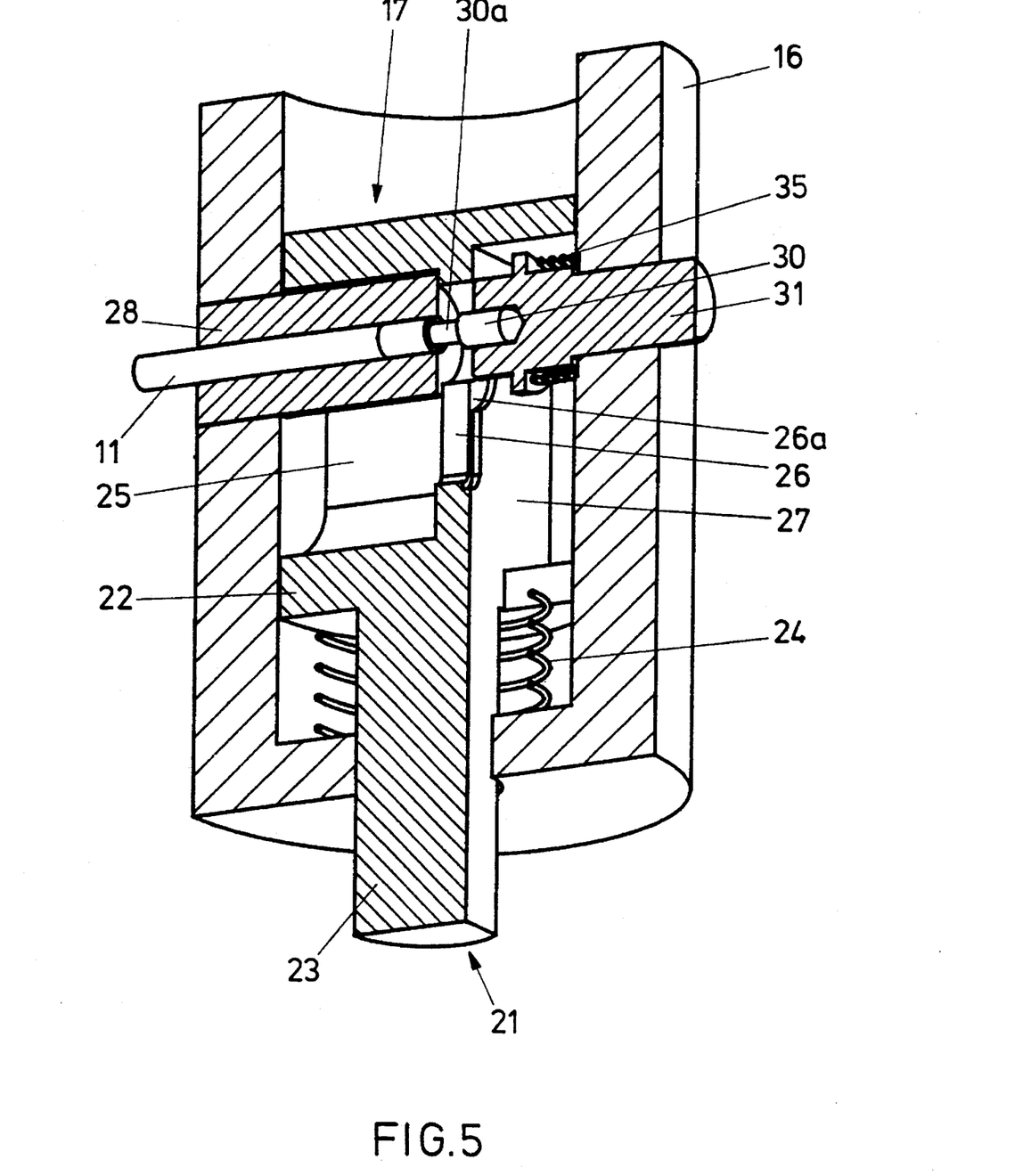
FIG. 5 shows the connector element according to FIG. 4 in a second assembly position.
Figure 6:
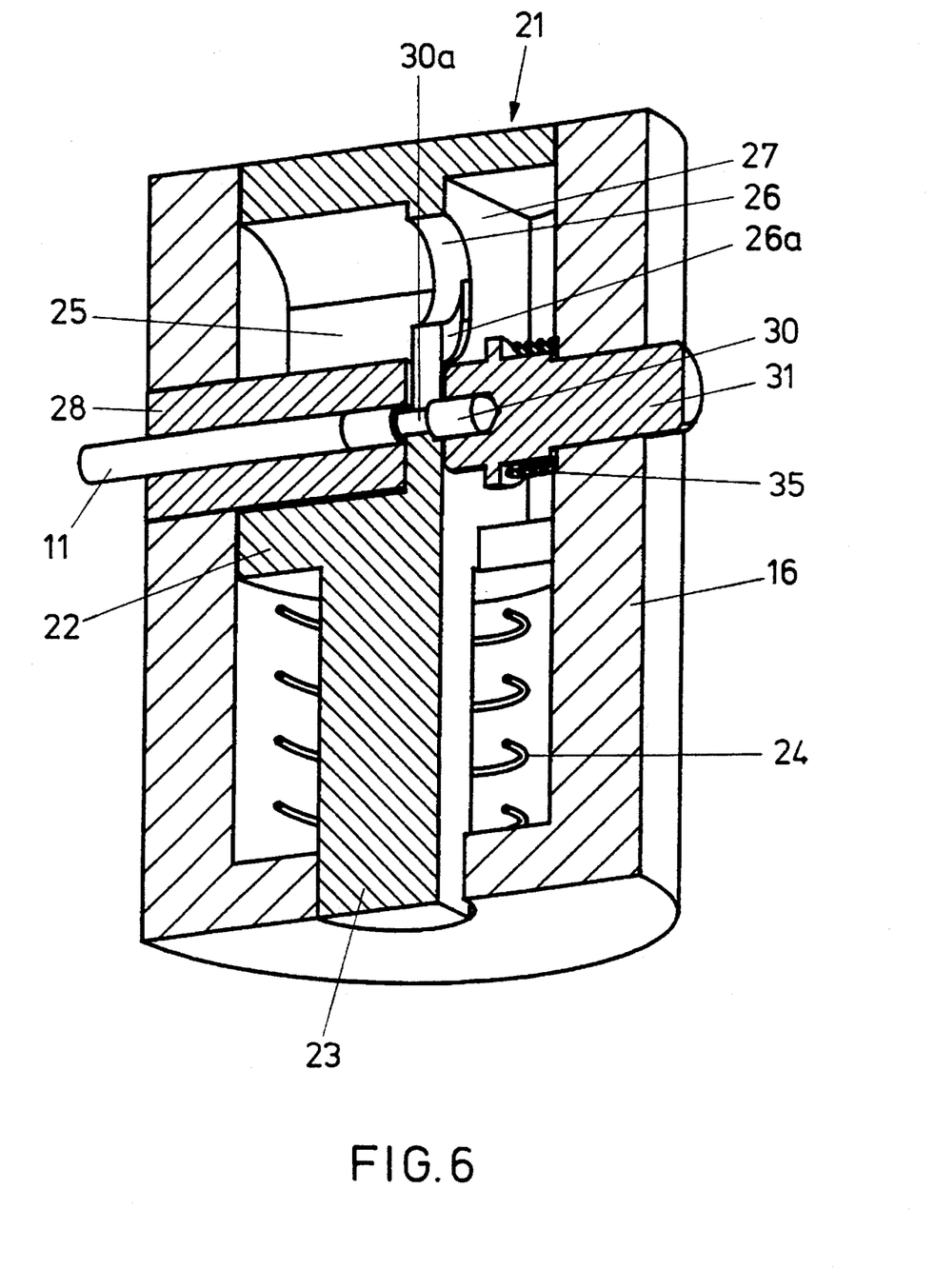
FIG. 6 shows the connector element according to FIG. 4 in a third embodiment.

The cylindrical part 22 is provided with a slotted hole-shaped recess 25 at right angles to its cylindrical wall, the bottom of this recess 25 being provided with a keyhole-shaped passage 26 and the central plane of the recess 25 and the passage 26 containing the centreline of the cylindrical member 22. The passage 26 terminates in a straight surface 27, which extends perpendicularly to the passage 26 and has been obtained by removing from the cylindrical member 22 a portion having a cross-section of a circular segment. When positioning the locking member 21 in the housing part 16, the slotted hole-shaped recess 25 should be aligned with the receiving bore 19, whereafter the locking member 21, albeit in resiliently movable manner, can be locked by inserting through the receiving bore 19 a shell 28 with a bore 29 for passing therethrough a cable 11 with an end 30 into the slotted hole-shaped recess 25. Before the locking member 21 is locked in the housing part 16 by means of the shell 28, first a stop member 31 with a stop bore 32, a collar 33 and a stop shoulder 34 has been inserted, with interposition of a spring 35, from the central bore 17 through the sliding bore 20. In assembled condition, the stop member 31 is pressed against the surface 27 by the spring 35, the centreline of the stop bore 32 coinciding with that of the bore 29 in the shell 28. With reference to FIGS. 4–6, now the insertion and locking of a cable 11 with end 30 in the connector element 15 will be discussed.

For fitting a cable 11, the cylindrical member 22 is pressed downwards against the force of the spring 24 to the extent where it abuts against the shell 28. In this position, through the action of the spring 35, the leading end of the stop member 31 is pushed through the part of the keyhole-shaped passage 26 of larger cross-section, so that the leading end of the stop member abuts against the end face of the shell 28. The fact that this position has been assumed can be visually deduced from the fact that the trailing end of the stop member 31 no longer projects relatively to the housing part 16.

Next, the cable 11 is inserted by its end 30 through the bore 29 into the shell 28 and pushed further until the end 30 strikes against the bottom of the stop bore 32, which is the position shown in FIG. 4.

By pushing the cable 11 further inwards, the stop member 31 is shifted against the force of the spring 35 into the position shown in FIG. 5, where the stop shoulder 34 abuts against the housing part 16 and a gap of the magnitude of the keyhole-shaped passage 26 is created between the shell 28 and the stop member 31, so that the locking member 21 no longer presses against the stop member 31 and can be pushed up by the spring 24.

The end 30 of the cable 11 is provided with a circumferential recess 30a, whose width is equal to the depth of the keyhole-shaped passage 26 and whose diameter can slide-fit into the narrower slotted part of the keyhole-shaped passage 26, so that the locking member 21, engaging in the recess 30a, can move further up and thereby grip the cable 11 at its end 30 so as to lock it, as shown in FIG. 6.

In order to locate the recess 30a in the space that has been created between the stop member 31 and the shell 28 as the stop member 31 is pushed back by the agency of the end 30 of the cable, the depth of the stop bore 32 and the length of the end 30 from the recess to the end face of end 30 must match. If the length referred to is too long, then, when the stop shoulder 34 abuts against the housing part 16, at least a part of the recess 30a will still be located within the bore 29, so that the narrower slotted part of the keyhole-shaped passage 26 cannot cooperate with the recess 30a, and the locking member 21 cannot be brought into the position where it locks cable 11. If the length referred to is too short, then at least a part of the recess will be situated within the stop bore 32, so that the narrower slotted part of the keyhole-shaped passage 26 cannot cooperate with the recess 30a, because opposite to a portion of the narrower slotted part of the keyhole-shaped passage 26, adjacent to the recess 30a, a portion will be located of larger diameter than the width of the slotted part. In this position, a part of the locking member 21 is located between the shell 28 and the stop member 31, so that this stop member remains in its position if the cable 11, carefully probing, were retracted. To prevent the possibility of the locking position being yet effected, a keyhole-shaped recess 26a is present, so shaped that in a situation as referred to in the previous full sentence, upon withdrawal of the cable 11, the stop member 31 can spring back until its leading surface abuts against the bottom of the keyhole-shaped recess 26a . As a result, the distance between shell 28 and stop member 31 is reduced and the locking member is locked against further upward displacement, so that the locking member 21 cannot move to the locking position, not even when the cable 11 has been retracted to the extent where the recess 30a and the narower slotted part of the keyhole-shaped passage 26 are in alignment.

As appears from FIG. 6, in the locking position of the locking member 21, the underside of the flattened cylindrical member 23 is located in the same plane as the underside of the housing part 16. If the locking member 21 cannot be brought into its locking position owing to the insertion of a cable 11 with a non-matching end 30, then the flattened cylindrical member 23 will project to a slightly lesser extent than shown in FIG. 5, which is a clear indication that it has been attempted to insert a wrong cable. A further safeguard against working with an unlocked or improperly locked cable 11 can be obtained by providing a stop within the housing 7, this stop preventing rotation of the drum 8 and hence displacement of the cable 11 when the flattened cylindrical member 23 projects from the connector element 15.

Figure 7:
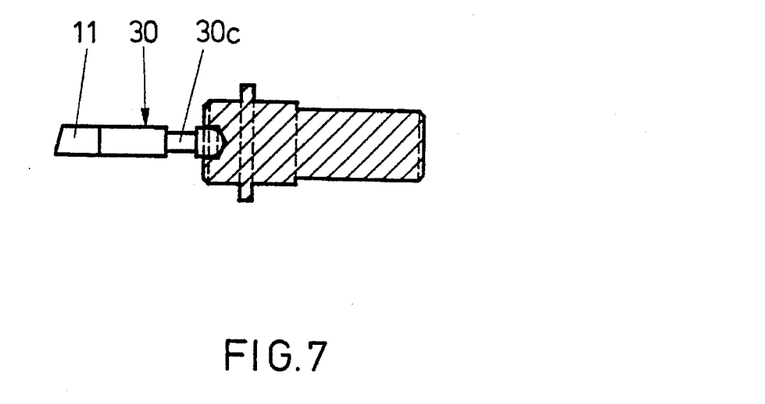
FIGS. 7–9 show three different cable ends each with an associated stop member for a connector element according to FIG. 4.
Figure 8:
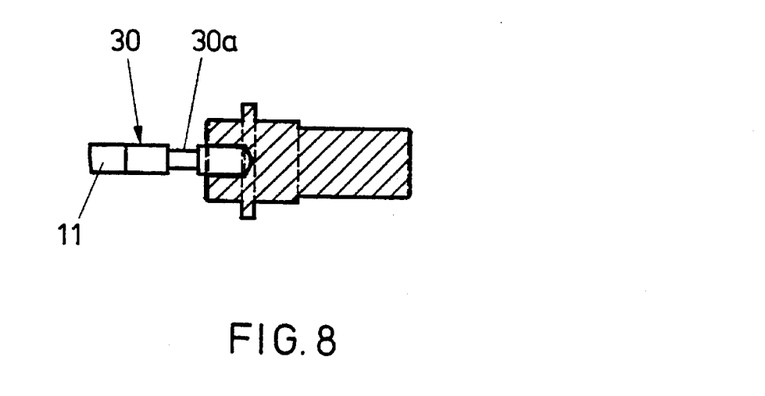
Figure 9:
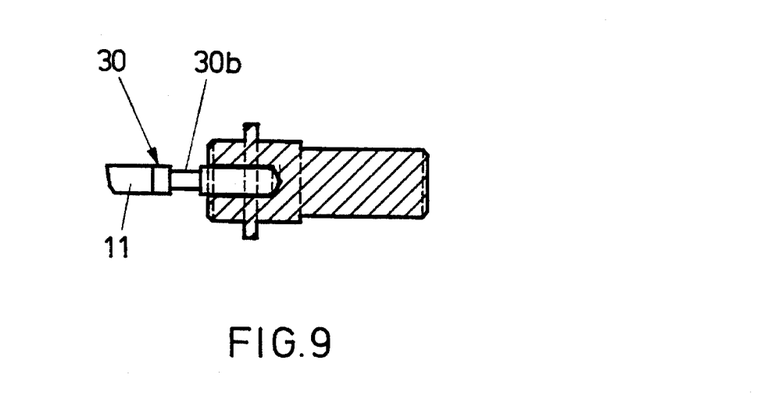

FIGS. 7–9 show a cable 11 with an end 30 each with a differently located recess 30c, 30a, and 30b, respectively, and a stop member adapted to the associated recess, i.e., a less deep or deeper bore for receiving the end 30. If it is assumed that the elements shown in FIG. 8 are used in FIGS. 4–6, then, upon insertion of a cable end with recess 30b into the connector element according to FIGS. 4–6, the situation will arise as described above, starting with the phrase: "If the length referred to is too long", whilst for the cable end with recess 30c, the passage starting: "If the length referred to is too short" applies.

Figure 10:
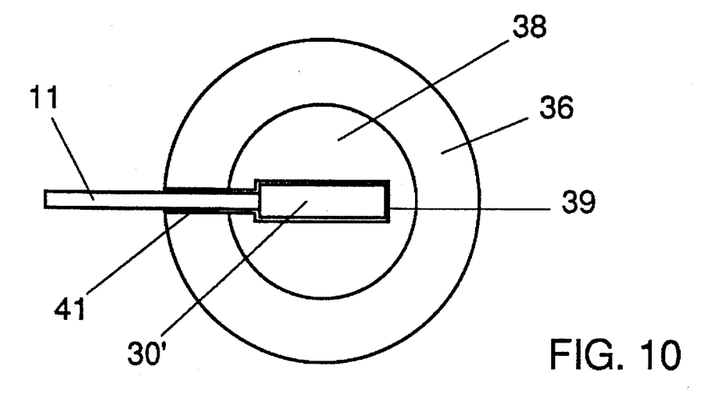
FIG. 10 shows a top plan view of a second, schematically shown embodiment of a connector element and a cable end.
Figure 11:
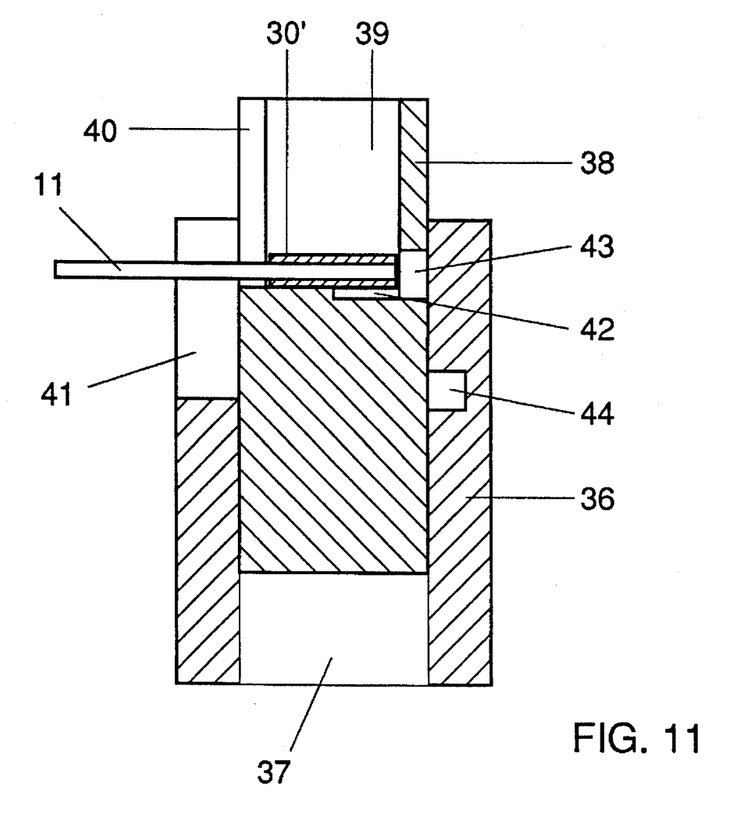
FIG. 11 shows a cross-section of the connector element according to FIG. 10 in a first assembly position.

FIGS. 10 and 11 schematically show a second embodiment of a connector element 15 for use in the drive unit 6 shown in FIG. 2. The connector element 15 comprises a housing part 36 with a central bore 37 into which a locking element 38 can be displaced with a sliding fit. The locking element 38 is provided with a recess 39, which matches the shape of the end 30' of a cable 11 to be received. The recess 39 is connected to the outer circumference of the locking element 38 through a slot 40 of a width equal to the diameter of the cable 11, the locking element having been guided into the housing part 36 such that the slot 40 connects to a slot 41 of equal width and provided in the housing part 36. At its lower end, the recess 39 is provided with a stepped recess 42 and a wall passage 43. Diametrically opposite the lower end of the slot 41, the housing part 36 is provided with a stop bore 44 whose cross-section is adapted to that of the end 30'.

Figure 12:
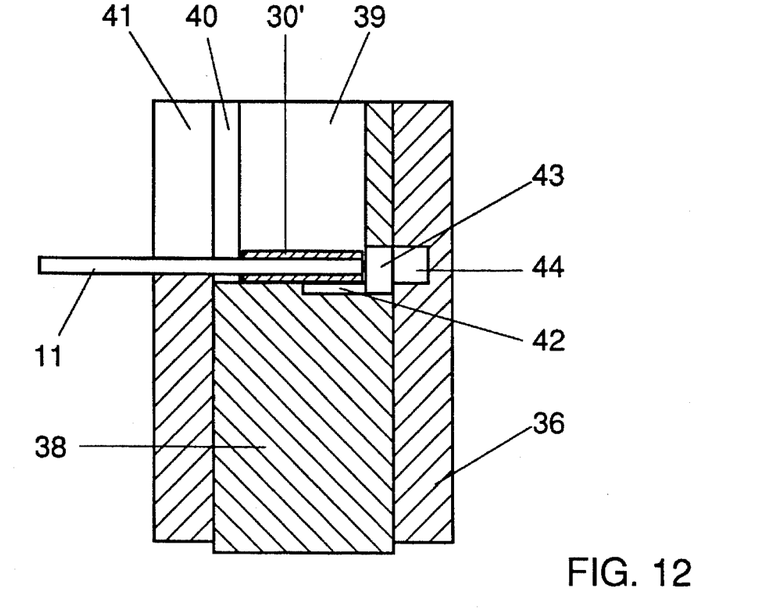
FIG. 12 shows the connector element according to FIG. 11 in a second assembly position.
Figure 13:
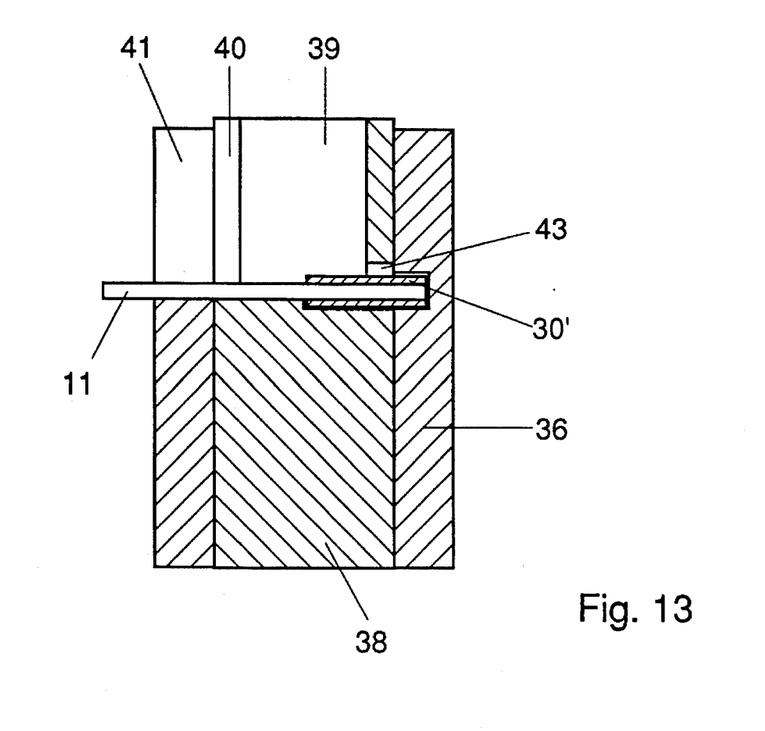
FIG. 13 shows the connector element according to FIG. 11 in a third assembly position.

For mounting a cable 11, the end 30' is fitted into the recess 39 and slid down until it abuts the bottom of the recess. It will be clear that the design of the end determines whether or not the end in question can be slipped in. After the position shown in FIG. 11 has been achieved in this manner, the locking element 38 is slid down until the position shown in FIG. 12 has been achieved. The cable 11 is subsequently slid further into the connector element in the lengthwise direction of the cable, the leading end of the end 30' ending up in the stop bore 44 via the wall passage 43 and abutting against the bottom of that bore. The stepped recess 42 is shaped such that the locking element 38 can be moved upwards so as to lock the cable in the connector element by engaging behind the end 30', as shown in FIG. 13.

It has already been observed that FIGS. 10–13 depict the connector element diagrammatically. It will be clear that, similarly to the embodiment shown in FIGS. 3–6, various stops can be present for controlling and limiting the displacement of the locking element 38 and that those displacements may be supported by spring action.

Figure 14:
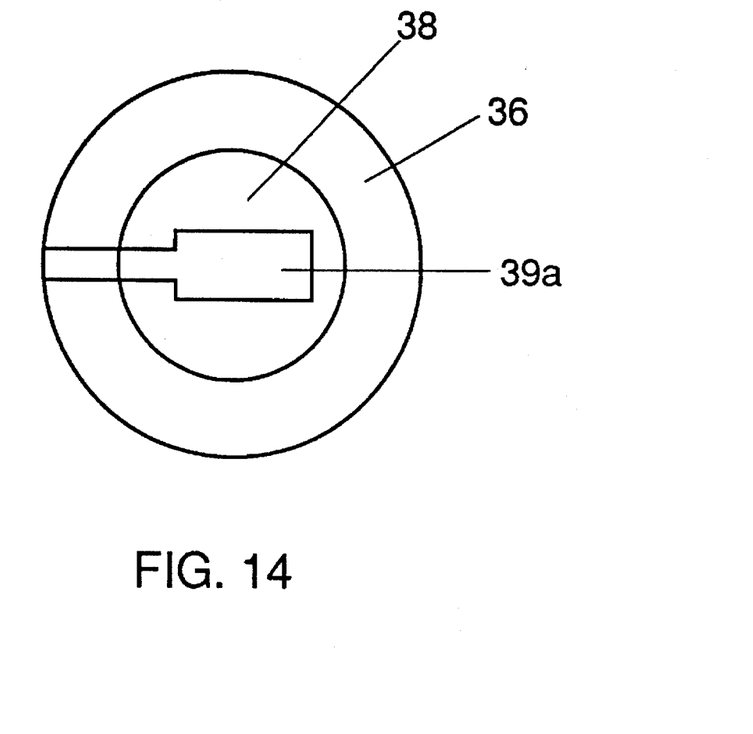
FIGS. 14 and 15 show a connector element according to FIG. 10 but each adapted to a differently designed cable end.
Figure 15:
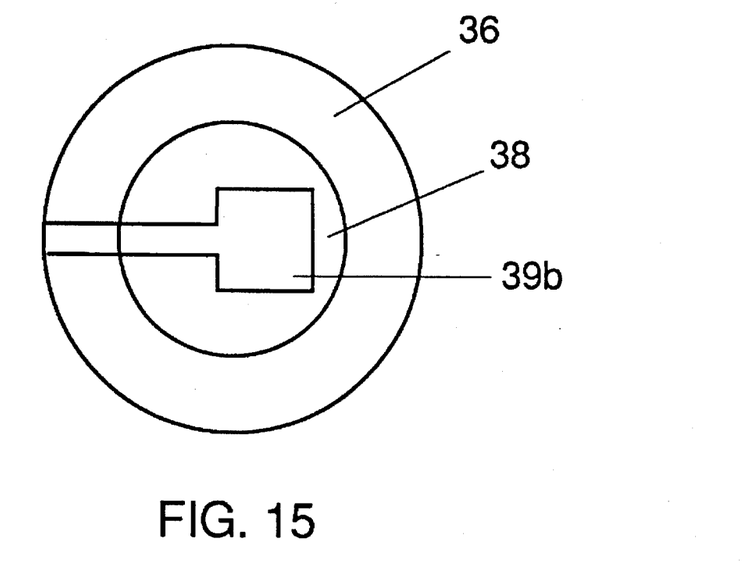

FIGS. 14 and 15, finally, show two further connector elements with recesses 39a and 39b in the locking element 38. It will be clear from FIGS. 10, 14 and 15 that the end 30' shown in FIG. 10 fits neither into the recess 39a nor into the recess 39b. Likewise, ends shaped according to recesses 39a and 39b, respectively, will not fit into the recesses 39 or 39b, and recesses 39 and 39a, respectively. The stop bore 44 shown in FIG. 11 will, in the embodiments according to FIGS. 14 and 15, have to be adapted to the cross-section of the end in question. Alternatively, each end may terminate in an identical part over the length of the stop bore, so that for all ends the same housing part can be used.

It will be clear that, within the concept of the invention as set forth in the accompanying claims, many modifications and variants are possible. To increase the range of different ends, it is possible, in addition to using different locations for the recesses and other shapes for the ends, to combine the two embodiments. One might also consider a range of ends all of the same basic shape and having the same collar projecting therefrom, this collar, however, being situated in different places on the basic shape.

I claim:

1. An apparatus for connecting one or more of each drive cable in a group of drive cables to a drive unit, wherein each drive cable of the group of drive cables has a first end with a first end part and a second end with a radioactive source attached thereto which is different from the radioactive source attached to each other cable of the group of cables, and wherein the first end part of each cable is receivable and lockable in connector elements of a group of connector elements for connecting the first end of each cable to the drive unit, such that each of the cables is drivable by the drive unit through a guide tube to a predetermined position for the different radioactive sources, the improvement comprising:

the first end part of each drive cable being of a mechanical configuration different from the mechanical configuration of the first end part of each other drive cable in the group of drive cables such that the different mechanical configuration of each end part is capable of identifying the different radioactive source attached to that each cable, the number of connector elements in the group of connector elements corresponding to the number of different end parts, each of the connector elements having locking means configured to receive and lock only a correspondingly configured end part, such that only a drive cable with a desired radioactive source can be received, locked and driven by a single connector element for that desired radioactive source.

2. An apparatus according to claim 1, wherein the locking means are formed by a stop member and a movable member such that the first end part is first positioned by the stop member and then locked in that position by the movable member.

3. An apparatus according to claim 2, wherein the mechanical configuration is formed by a circumferential recess provided in the first end part, the distance from the recess to a free end of the first end part constituting the mechanical configuration of the first end part to identify the radioactive source; the stop member of the locking means is provided with a bore, which has a cross-section such that the first end part can be received therein with a sliding fit and has a depth which determines which identified first end part can be locked by the locking means; and the movable member of the locking means is formed by a guided element capable of moving transversely to the bore and having a part with a width substantially corresponding to the length of the circumferential recess in the first end part and comprising a slot, open at one end, of a width corresponding to the diameter of the first end part at the recess, the locking of the first end part being effected by inserting the first end part into that bore until it is stopped, and subsequently moving the movable member such that the recess in the first end part comes to lie in the slot, whereby the first end part is locked in the position wherein it has been stopped in the bore.

4. An apparatus according to claim 1, wherein location and displacement of the locking means of all connector elements are equal and a dimension of bores in the connectors is different for each connector element.

5. An apparatus according to claim 4, wherein a diameter of the bores is equal in all connector elements and the depth of the bores is different in each connector element.

6. An apparatus according to claim 5, wherein the mechanical configuration comprises a circumferential recess, which can cooperate with an open slot in a part of the locking means, which part can be moved in the longitudinal direction of the open slot between a position outside a path of the first end part and a position wherein that first end part is locked with a bottom of the open slot which engages in the recess so as to lock said first end part.

7. An apparatus according to claim 6, wherein the circumferential recess is provided in a cylindrical element at a distance from a free end thereof, that distance, together with the depth of the bore, determining whether or not the recess and the open slot can cooperate for locking action.

8. An apparatus according to claim 7, wherein a stop member is resiliently mounted so as to be movable in the longitudinal direction of the bore between a resiliently decompressed position and a resiliently compressed position.

9. An apparatus according to claim 8, wherein the locking means comprising the part provided with the open slot is resiliently mounted in the connector element so as to be movable in the longitudinal direction of the open slot, the stop member being located outside the path of the locking means in the resiliently compressed position and in the path of the locking means in the resiliently decompressed position.

10. An apparatus according to claim 9, wherein the locking means is provided with a pawl-shaped part, which forms a projection of the connector element when the bottom of the open slot is not in locking cooperative engagement with the recess, and which does not form a projection of the connector element when the bottom of the open slot is in locking cooperative engagement with the recess, the pawl-shaped part in its projecting position blocking the normal operation of the drive unit.

* * * * *

UNITED STATES PATENT AND TRADEMARK OFFICE
CERTIFICATE OF CORRECTION

PATENT NO. : 5,503,041  
DATED : April 2, 1996  
INVENTOR(S) : Eric VAN'T HOOFT

Page 1 of 2

It is certified that error appears in the above-identified patent and that said Letters Patent is hereby corrected as shown below:

IN THE CLAIMS:

Column 8, line 6, after "each", insert --type of--.

Column 8, line 7, after "group of", insert --types of--.

Column 8, line 8, change "the group" to --a type--.

Column 8, line 11, change "other" to --drive--; change "the group" to --another type--; and before "cables,", insert --drive--.

Column 8, line 12, after "each", insert --drive--.

Column 8, line 14, after "each", insert --drive--.

Column 8, line 15, after "each of the", insert --drive--.

Column 8, line 19, after "drive cable", insert --of a type of drive cables--.

UNITED STATES PATENT AND TRADEMARK OFFICE
CERTIFICATE OF CORRECTION

PATENT NO. : 5,503,041
DATED : April 2, 1996
INVENTOR(S) : Eric VAN'T HOOFT

It is certified that error appears in the above-identified patent and that said Letters Patent is hereby corrected as shown below:

Column 8, line 21, delete "in the".

Column 8, line 22, change "group" to --of each other type--.

Column 8, line 24, after "each", insert --drive--.

Signed and Sealed this

Nineteenth Day of August, 1997

*Attest:*

BRUCE LEHMAN

*Attesting Officer*   *Commissioner of Patents and Trademarks*